United States Patent [19]

Bhattacharva et al.

[11] Patent Number: 5,288,853

[45] Date of Patent: Feb. 22, 1994

[54] FACTOR VIII PURIFICATION PROCESS

[75] Inventors: Prabir Bhattacharva, Walnut; Toshiharu Motokubota, Arcadia, both of Calif.

[73] Assignee: Alpha Therapeutic Corporation, Los Angeles, Calif.

[21] Appl. No.: 876,410

[22] Filed: Apr. 30, 1992

[51] Int. Cl.$^5$ .................. A61K 35/14; C07K 13/00
[52] U.S. Cl. ............................ 530/383; 530/413; 530/415; 530/419; 530/420
[58] Field of Search ............. 530/383, 413, 415, 419, 530/420

[56] References Cited

U.S. PATENT DOCUMENTS

| | | | |
|---|---|---|---|
| Re. 32,011 | 10/1985 | Zimmerman et al. | 99/293 |
| 3,682,881 | 8/1972 | Fekete et al. | 530/383 |
| 4,361,509 | 11/1982 | Zimmerman et al. | 530/383 |
| 4,543,210 | 9/1985 | Mitra et al. | 530/383 |
| 4,758,657 | 7/1988 | Farb et al. | 530/413 |
| 5,110,907 | 5/1992 | Kosow et al. | 530/383 |

FOREIGN PATENT DOCUMENTS

| | | |
|---|---|---|
| 806300190 | 6/1980 | European Pat. Off. |
| 903081040 | 7/1990 | European Pat. Off. |

OTHER PUBLICATIONS

Saundry et al., "Chromatography of vWF on Dextran Sulphate Sepharose", *Thrombosis Research*, 48, 641–652 (1987).

Harrison et al., "Chromatography of the VIII/vWF Complex on Dextran Sulphate Sepharose", *Thrombosis Research*, 50, 295–304 (1988).

Roberts et al., "von Willebrand Factor Binds Specifically to Sulfated Glycolipids", *J. Biol. Chem.*, 261, 3306–3309 (1986).

Hamer et al., "Human factor VIII: purification from commercial factor VIII concentrate, characterization, identification and radiolabeling", *Biochim. et Biophys. Acta*, 873, 356–366 (1986).

Madaras et al., "Isolation and Insolubilisation of Human F VIII by Affinity Chromatography", *Haemostasis*, 7, 321–331 (1978).

Flow Charts I and II, which relate to processes previously used for producing Factor VIII.

*Primary Examiner*—Howard R. Schain
*Assistant Examiner*—Lynn Touzeau
*Attorney, Agent, or Firm*—Christie, Parker & Hale

[57] ABSTRACT

There is provided in accordance with the practice of this invention a process for separating Factor VIII complex from an impure protein fraction containing Factor VIII complex. An aqueous solution of the impure protein fraction containing Factor VIII complex is applied to a heparin-coupled chromatographic medium, to bind the Factor VIII complex to the medium. The Factor VIII is then recovered from the heparin-coupled chromatographic medium by elution with an aqueous solution comprising $CaCl_2$ and histidine. The recovered Factor VIII is further purified by precipitation with a solution comprising glycine and NaCl, and washing the resultant precipitate with a solution comprising histidine, glycine, and NaCl to provide a Factor VIII complex solution with a specific activity of about 70 to about 150 units/mg.

21 Claims, 2 Drawing Sheets

FACTOR VIII PURIFICATION PROCESS

FIELD OF THE INVENTION

This invention relates to an improved process for preparing Factor VIII concentrates.

BACKGROUND OF THE INVENTION

Coagulation of blood is a complex process requiring the sequential interaction of a large number of components, nearly all of which are proteins. These components include fibrinogen and Factors II, V, VII, VIII, IX, X, XI, and XII. A lack of any of these components, or a nonfunctional component, can lead to an inability of the blood to clot when required, with resultant excessive and life-threatening blood loss to the patient.

Factor VIII is absent or is present at deficient levels in certain individuals. For example, persons who have a deficiency (or absence) of Factor VIII, i.e., persons suffering from hemophilia A, have blood which either fails to clot or clots only after longer periods of time than the time required for clotting in a person who has a normal level of Factor VIII.

Factor VIII is present in plasma as a high-molecular-weight complex (Factor VIII complex), which includes Factor VIII:C and von Willebrand factor (Factor VIII:RAg or vWf). Factor VIII:C promotes blood coagulation. Factor VIII:RAg interacts with platelets to promote aggregation of the platelets and, when incorporated in the Factor VIII complex, acts as a stabilizer for Factor VIII:C.

The primary therapeutic use of Factor VIII has been its intravenous administration to hemophilia A patients. In severe cases, relatively high concentrations of Factor VIII are required. These high concentrations are obtained by purification and concentration of Factor VIII. However, purification often leads to instability and loss of Factor VIII:C activity because of the removal of Factor VIII:RAg from the Factor VIII complex during purification. Thus, the resultant purified product is often a mixture of both stable Factor VIII complex and unstable Factor VIII:C, along with contaminating proteins that have not been removed.

Some processes for producing Factor VIII concentrate have been based on a discovery by Poole et al. (*Nature*, 203, p. 312 (1964)) that the precipitate remaining after plasma is frozen and then thawed, i.e., the cryoprecipitate, contains Factor VIII in a concentrated form and excludes various other protein fractions. It was discovered that, in addition to Factor VIII, the cryoprecipitate also includes the major portion of the fibronectin component of plasma.

Work progressed over the years to perfect the separation of Factor VIII from other proteins in the cryoprecipitate, including the fibronectin component, so that the resultant products would incorporate increased concentrations of Factor VIII relative to the other proteins present in the plasma.

One area in which a substantial amount of work has been done in the production of Factor VIII is based on the use of polyethylene glycol (PEG) to precipitate Factor VIII from other proteins in an aqueous cryoprecipitate solution. For example, U.S. Pat. No. 3,652,530, which issued on Mar. 28, 1972 to A. J. Johnson, discloses a process for preparing a Factor VIII concentrate by fractionating cryoprecipitate with PEG at a relatively lower concentration to precipitate fibrinogen and other proteins, and then increasing the PEG concentration to precipitate Factor VIII.

U.S. Pat. No. Re. 29,698 to Fekete et al. discloses a process for production of Factor VIII by which heparin is added to a cryoprecipitate solution, along with PEG, to provide increased yields of precipitated Factor VIII. It is disclosed that the amount of heparin employed during the fractionation step can vary, with the optimum concentration being one unit of heparin per ml of the plasma solution, whereas concentrations of heparin greater than about 10 units per ml are to be avoided as dangerous.

Purification of Factor VIII by chromatography on heparin (European Patent Application. No. 90308104.0 to Battacharya et al. and Madras et al., *Haemostasis*, 7, 321-331 (1978)) has also been used. The Madras process, while producing Factor VIII complex, results in a Factor VIII complex with little or no activity. The Battacharya process results in an active Factor VIII; however, the specific activity of the protein purified was at best 66 units/mg. (The phrase "specific activity" as used herein means units of Factor VIII:C clotting activity per milligram of protein. A "unit" is defined as the amount of Factor VIII:C in one ml of normal plasma.)

Purification of Factor VIII has also been achieved by chromatography on monoclonal antibody-containing chromatography media (U.S. Pat. Nos. 4,361,509 and Re. 32,001 to Zimmerman et al.). Such procedures result in Factor VIII:C of very high specific activities, approximately 1500 to 2500 units/mg of total protein, and, therefore, high purity. However, in the Zimmerman process, the Factor VIII:RAg is dissociated from Factor VIII:C, which results in the Factor VIII:C being unstable.

Currently, the methods used to purify Factor VIII result in protein preparations, i.e., Factor VIII concentrates, which have a relatively low Factor VIII:C specific activity. It is desirable that there be provided an improved process for the separation of Factor VIII complex, i.e., the intact Factor VIII:C/Factor VIII:RAg complex, from contaminating proteins for producing Factor VIII which results in increased purity, higher concentration, and enhanced yields and stability of the protein.

SUMMARY OF THE INVENTION

The present invention is directed to a process for separating Factor VIII complex from an impure protein fraction containing Factor VIII complex, for example, from a plasma fraction or from any recombinant-DNA or transgenic-derived materials containing Factor VIII complex. The Factor VIII complex is separated by applying the impure protein fraction to a heparin-coupled chromatographic medium, binding Factor VIII complex to the heparin, and then eluting the Factor VIII complex from the chromatographic medium using an aqueous solution comprising $CaCl_2$ and histidine. The Factor VIII complex is further purified by precipitating the Factor VIII complex from the eluate with glycine and sodium chloride and washing the precipitate with a wash solution. The Factor VIII complex precipitate is then dissolved in an aqueous solution to provide a Factor VIII complex solution with a specific activity of about 100 to about 150 units/mg.

BRIEF DESCRIPTION OF THE DRAWING

These and other features and advantages of the present invention will become better understood with reference to the following description, appended claims, and accompanying drawings, wherein:

FIGS. 1 and 2 are flow charts illustrating an exemplary embodiment of a process provided in accordance with practice of the present invention for preparing a Factor VIII complex concentrate from blood plasma.

DETAILED DESCRIPTION

Figure 1A:
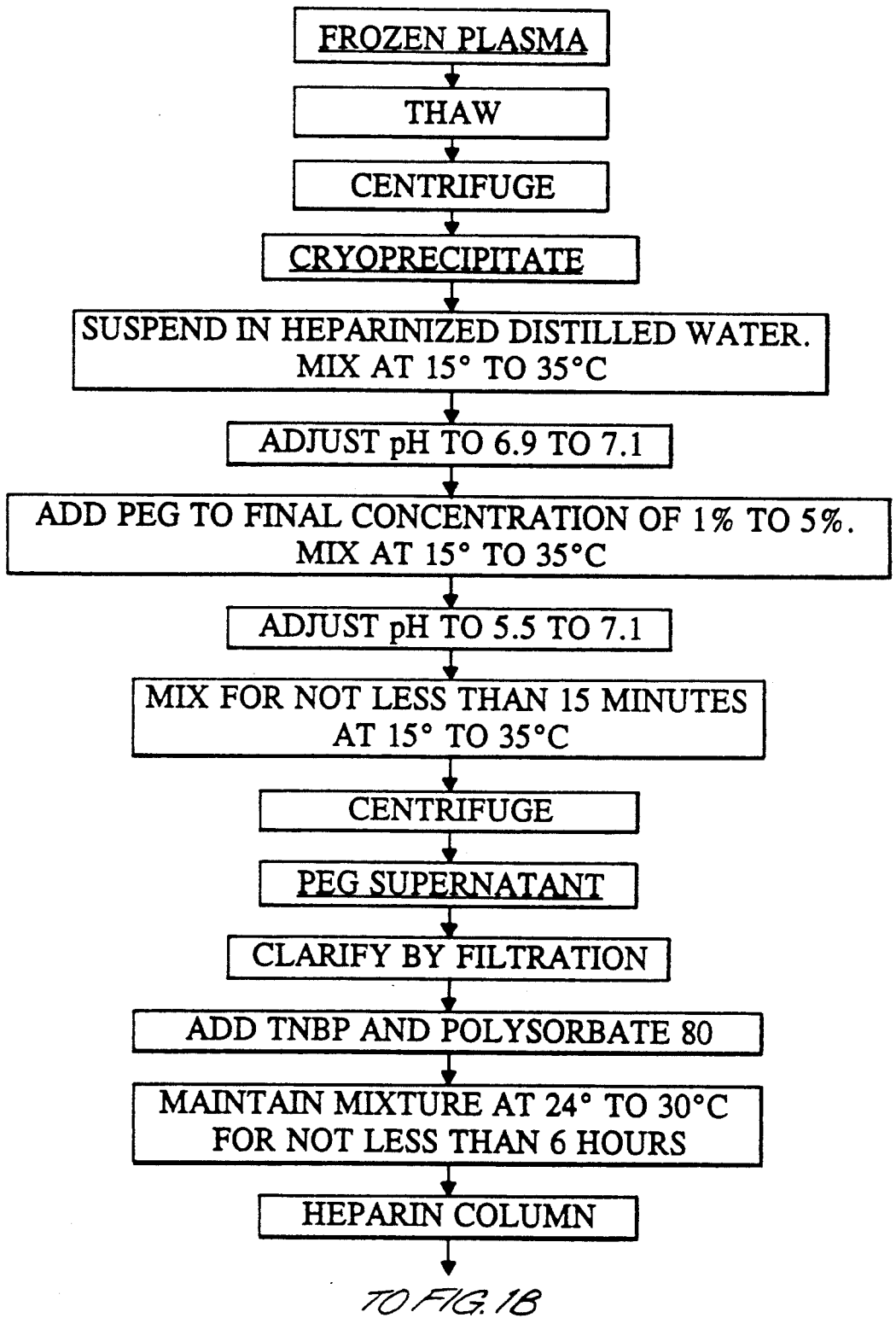
Figure 1B:
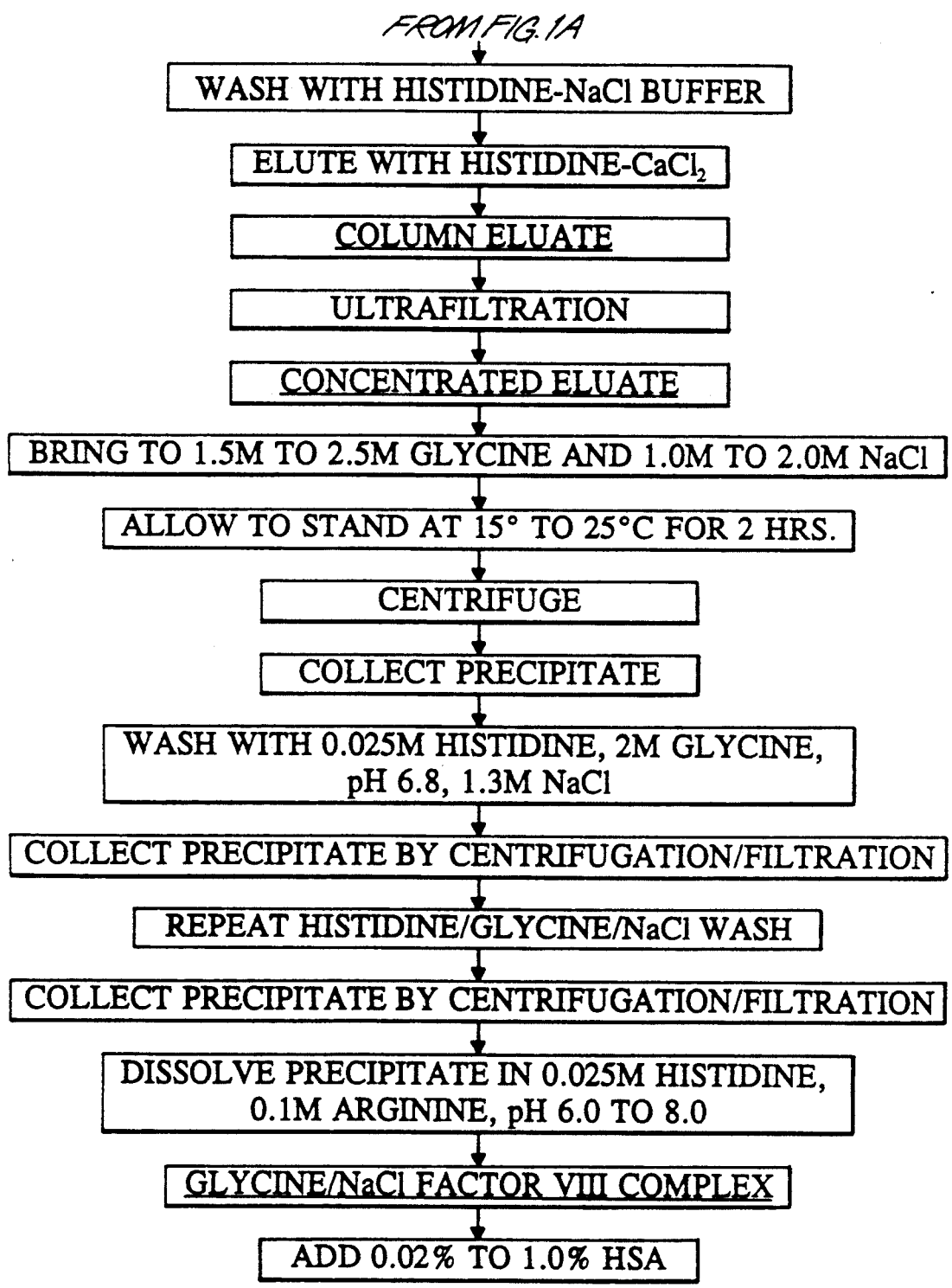

The process of this invention provides a simple and efficient purification method for high-specific-activity Factor VIII complex from an impure protein fraction. The phrase "impure protein fraction" as used herein means a solution which contains one or more protein(s) in addition to Factor VIII complex, where removal of these additional proteins is desired. The impure protein fraction used as the starting material for the purification of Factor VIII complex may be derived from a variety of sources, such as cryoprecipitate or other blood plasma-derived fractions, or it may be derived by recombinant-DNA or transgenic techniques. Briefly, the Factor VIII complex is purified by PEG precipitation step results in a, in the presence of heparin, then by chromatography on a heparin chromatography medium. The final step in the purification is to precipitate the Factor VIII complex in the presence of glycine and sodium chloride. The addition of the glycine/NaCl precipitation 1.5 to 2 fold increase in the specific activity of the Factor VIII:C complex over prior art purification methods. A detailed description of the purification procedure is set out below.

Preparation of An Impure Protein Fraction

In one exemplary embodiment of the practice of this invention, the starting material for providing the impure protein fraction comprising Factor VIII complex is cryoprecipitate. The cryoprecipitate is recovered from human blood plasma that has been collected and tested according to procedures approved by the U.S. Food and Drug Administration. The plasma is frozen at a temperature of about $-20°$ C., and is subsequently thawed at $0°$ C. to $5°$ C. During the thawing process, a precipitate forms (the "cryoprecipitate") which is removed by centrifugation and recovered for further purification and concentration.

The cryoprecipitate is dissolved in a "heparin solution" which comprises distilled water and from about 30 to 150 units of heparin per ml of water at a pH of about 6.0 to about 8.5. In an exemplary embodiment, 80 units of heparin per ml of water, at pH 7.5, is used. The solution is then mixed at a temperature of from about $15°$ C. to about $35°$ C. until the cryoprecipitate is completely dissolved (approximately 10 minutes), to provide a cryoprecipitate/heparin solution. Preferably, the temperature during mixing is maintained at about $30°$ C., and the volume of heparin solution used is from about 2 to about 10 liters per kilogram of cryoprecipitate. After the cryoprecipitate is dissolved, the pH of the cryoprecipitate/heparin solution is adjusted to about 6.9 to 7.1 using, for example, 0.1M HCl, and the solution is stirred for an additional 20 to 30 minutes.

One unit of heparin is defined to mean one U. S. P. (United States Pharmacopoeia) unit. The U. S. P. unit of heparin is that quantity required to prevent 1.0 ml of citrated sheep plasma from clotting for one hour after the addition of 0.2 ml of a 1:100 calcium chloride ($CaCl_2$) solution. The term "heparin" as used herein is meant to include heparin itself and the pharmaceutically-acceptable, water-soluble salts of heparin, e.g., the sodium salts. A suitable example of a commercially-available heparin sodium product is U. S. P. heparin from Lyphomed Company, of Melrose Park, Ill., or from Sigma Chemical Company (Sigma No. H7005), of St. Louis, Mo.

Polyethylene glycol (PEG), preferably having a molecular weight in the range of from about 2000 to about 6000 (more preferably, from about 3000 to about 4000), is then added to the cryoprecipitate/heparin solution to provide a PEG solution having a final PEG concentration of from about 1% to about 5% (wt/vol). The term "% (wt/vol)" as used herein means the weight of material added per 100 ml of starting volume of solution. The percentages referred to herein are all weight-per-volume, unless otherwise indicated. Preferably, the PEG is added in the form of a solution prepared by dissolving the PEG in distilled water which comprises a citrate salt (such as sodium citrate). In one exemplary embodiment, the aqueous PEG solution, added to the cryoprecipitate/heparin solution, comprises about 31.5% (wt/vol) PEG, 0.22% (wt/vol) sodium citrate dihydrate, and 0.08% (wt/vol) citric acid monohydrate at a pH of 6.2. The pH of the PEG solution is adjusted to between 5.5 to 7.1 with an acid such as dilute acetic acid. In one exemplary embodiment, the pH is about 6.3. The pH-adjusted PEG solution is mixed for at least about 15 minutes, at a temperature of from $15°$ C. to $35°$ C. In one embodiment, the temperature is about $27°$ C.

The addition of 1% (wt/vol) to 5% (wt/vol) PEG (preferably, 3% (wt/vol) to 5% (wt/vol)) to form the PEG solution results in precipitation of various proteins such as fibronectin and fibrinogen, leaving Factor VIII complex in solution. The fibronectin and other precipitated proteins, i.e., the PEG precipitate, are separated from the Factor VIII complex-comprising solution (the PEG supernatant) by centrifugation. The PEG supernatant, i.e., the Factor VIII complex comprising impure protein fraction, is recovered and processed further, in accordance with the process of this invention, to purify Factor VIII complex.

The PEG supernatant solution, i.e., the Factor VIII complex comprising impure protein fraction, is clarified by filtration and then further processed, for purification of Factor VIII complex, by affinity chromatography.

In an exemplary embodiment of practice of this invention, the Factor VIII complex production process includes steps for inactivating viruses that may be present in such blood products, e.g., hepatitis B virus, hepatitis non-A/non-B virus, HIV (AIDS virus), Cytomegalovirus, Epstein-Barr virus, and the like, prior to the affinity chromatography step. In one embodiment, a solution comprising both an organic solvent and a detergent, is added to the PEG supernatant to inactivate virus that may be present. The amount of organic solvent and detergent added preferably results in a solution comprising about 0.3% (wt/vol) organic solvent and about 1% (wt/vol) detergent. A detergent useful in practice of principles of the invention is one sold by under the trademark "TWEEN-80" by Fisher Scientific, of Springfield, N.J.; another is a detergent sold under the trademark "TRITON X-100," by Aldrich Company, of Milwaukee, Wis. Useful organic solvents are tri-n-butyl-phosphate (TNBP), ethyl ether, and the like. The solution is incubated for about 6 hours to about 7 hours, at a temperature of from about 24° C. to about 30° C. Inactivation of virus using organic solvent/detergent mixture is described in U.S. Pat. No. 4,540,573, which issued on Sep. 10, 1985 to Neurath et al., and which is incorporated herein by this reference.

Preparation of Heparin-Coupled Chromatographic Medium

Preparation of the heparin-coupled chromatographic medium is achieved in accordance with this invention by coupling heparin or heparin sulfate to an activated resin. Activated resins useful in the practice of this invention include, but are not limited to, cyanogen bromide-activated agarose, N-hydroxy succinimide-activated agarose, aldehyde-activated agarose, cyanogen bromide-activated sepharose, cyanogen bromide-activated silica, and the like.

In one exemplary embodiment of preparing a heparin-coupled chromatographic medium, heparin is bound to an activated aldehyde-agarose resin supplied by Sterogene Biochemicals, of Arcadia, Calif., under the trademark "ACTIGEL-A." In this embodiment, the ACTIGEL-A is washed and equilibrated in 3 volumes of a buffer, such as phosphate, acetate, or borate buffers, at concentrations of about 0.1 molar (M), and at a pH of from about 6.5 to about 7.5. A coupling mixture of heparin in a buffer comprising about 0.1M phosphate, acetate, or borate with about 0.1M sodium cyanoborohydride ($NaCNBH_3$), at a pH of from about 6.5 to about 7.5, is added to an equal volume of washed ACTIGEL-A resin and incubated for 12 to 20 hours at about 4° C. to about 30° C. with constant agitation on a mechanical mixer, such as a Labquake rotary tumbler supplied by Scientific Products, of Irvine, Calif. After coupling, the mixture is filtered in a Buckner funnel, using a medium-gauge, scintered-glass filter, and the retentate, i.e., the heparin-coupled/ACTIGEL-A chromatographic medium, is washed by pouring several volumes of a solution comprising about 0.1M phosphate, acetate, or borate buffer, at about pH 6.5 to 7.5, comprising 0.5M to 1M NaCl, through the retentate while in place on the Buckner funnel. The washed heparin-coupled chromatographic medium is then incubated at 4° C. to 30° C. in about 0.1M ethanolamine, at about pH 6.5 to 7.5, for about two hours, to deactivate any unreacted aldehyde groups. The heparin-coupled chromatographic medium is filtered in a Buckner funnel, using a medium-gauge, scintered-glass filter, and then washed by pouring several volumes of a solution containing about 1M NaCl through the heparin-coupled chromatographic medium while in place on the Buckner funnel. Finally, the medium is washed with a buffer, such as a phosphate buffer, at a concentration of about 0.1M, at about pH 6.5 to 7.5. The heparin-coupled chromatographic medium is then stored, refrigerated at about 4° C. to 10° C., in about 0.1M phosphate buffer, pH 6.5 to 7.5, with about 0.01M sodium azide or other bactericide added as a preservative.

The amount of heparin used in the coupling reactions is preferably from about 250 to about 2000 units of heparin per ml of ACTIGEL-A, and is more preferably about 1000 units of heparin per ml of ACTIGEL-A, since this concentration gives optimal binding of Factor VIII complex. At concentrations below about 1000 units per ml, there are undesirably high concentrations of Factor VIII complex found in the chromatography effluent. At concentrations greater than 1000 units of heparin per ml, there is no increase in the amount of Factor VIII complex bound, and, therefore, the additional heparin would add unnecessarily to the cost of the process.

Preparation of The Chromatography Column

In one embodiment of practice of the process of the invention, chromatographic columns such as those supplied by Amicon Corporation, of Danvers, Mass., are used. The heparin-coupled chromatographic medium prepared as described above is decanted from the sodium azide preservative solution, in which it is stored, and washed with a buffer, such as histidine, comprising from about 0.015M to about 0.035M histidine, at a pH of about 6.5 to 7.5. The heparin-coupled chromatographic medium is slurried with a sufficient volume of buffer, such as 0.015M to 0.035M histidine, pH 6.5 to 7.5, so that the slurry volume does not exceed the total column volume, and the slurry is not so thick as to retain air bubbles. The bottom of the column is filled with from about 1 to about 3 centimeters of a solution comprising a buffer, such as 0.015M to 0.035M histidine, at about pH 6.5 to 7.5, comprising about 0.1M to 0.15M of a salt, such as NaCl, LiCl, or KCl, at the temperature at which the column is to be run. The slurried chromatographic medium is then packed into the column by pouring it down the side wall, to provide a heparin-coupled chromatography column useful in the practice of this invention to separate Factor VIII complex from the impure protein fraction containing Factor VIII complex.

If desired, in accordance with the techniques of this invention for separation of Factor VIII complex from the impure protein fraction, the heparin-coupled chromatographic medium can be used in a batch, rather than a column, process. In the batch process, the heparin-coupled chromatographic medium prepared as described above is decanted from the sodium azide solution in which it is stored and is washed with a buffer, such as histidine, at a concentration of about 0.015M to about 0.035M, at a pH of about 6.5 to 7.5. The buffer solution is decanted, and the washed heparin-coupled chromatographic medium is added directly to the Factor VIII complex containing impure protein fraction.

Separation of Factor VIII Complex by Affinity Column Chromatography

In an exemplary embodiment of the practice of this invention, Factor VIII complex solution from the viral inactivation step (the Factor VIII complex containing impure protein fraction) is applied to the chromatography column containing a heparin-coupled chromatographic medium by pouring the solution through the column. While the cross-linker agarose resin is preferred, other heparin or heparin sulfate-coupled media are also suitable for practice of this invention. Other dextran sulfate compounds coupled to a chromatography medium would also be useful in the purification process. The flow rate of the column is about 0.35 ml per min. for a small (about 5 ml) column, to about 2 ml per min. for a large (about 50 ml) column. As the impure protein fraction flows through the column, Factor VIII complex binds to the heparin ligand on the heparin-coupled chromatographic medium, while other proteins pass through the chromatographic medium in the column and flow from the column as effluent. Preferably, no more that about 20 units of Factor VIII:C activity are applied to the column per ml of heparin-coupled chromatography medium in the column when, as in one exemplary embodiment, 1000 units of heparin are bound per ml of activated resin. When greater than about 20 units of Factor VIII:C activity are added per ml of heparin-coupled chromatographic medium, the excess Factor VIII complex is not bound, but is instead washed through the column into the column effluent. If less than about 20 units of Factor VIII:C activity per ml are added, the maximum binding capacity of the heparin-coupled chromatographic medium (at 1000 units of heparin per ml of activated resin) is not being used.

The heparin-coupled chromatographic medium with Factor VIII complex bound to it is washed to remove all unbound proteins. In one exemplary embodiment, the washing is effected by applying about 5 to 10 volumes of a solution comprising about 0.015M to 0.035M buffer, such as histidine, pH 6.5 to 7.5, comprising about 0.1M to 0.15M of a salt solution, such as LiCl, NaCl, or KCl, and the effluent from the column is discarded. Preferably, the solution comprises 0.025M histidine at a pH of 6.8 with 0.15M NaCl. Histidine is preferred as a buffer in the purification, since the final lyophilized Factor VIII is more easily resolubilized when it is in a buffer comprising histidine. However, while histidine is preferred, other buffers known in the art could be used. Where buffers other than histidine are used during the purification, it is preferable that the final purified Factor VIII is transferred into a buffer comprising histidine prior to lyophilization, by dialysis or other suitable method. The Factor VIII complex remains bound to the chromatographic medium throughout the wash procedure.

Factor VIII complex is eluted from the column, i.e., from the heparin-coupled chromatographic medium, by applying to the column a buffered aqueous solution incorporating calcium, magnesium, strontium, or other divalent metal-ion salt, such as $CaCl_2$, $MgCl_2$, $SrCl_2$, or the like, and histidine. Preferably, the eluting agent is $CaCl_2$ at a concentration of from about 0.01M to about 0.3M, and about 0.015M to about 0.035M histidine. More preferably, the $CaCl_2$ is at a concentration of from about 0.05M to about 0.2M, and the histidine concentration is from about 0.02M to about 0.03M, and most preferably, the $CaCl_2$ is at a concentration of about 0.1M, and the histidine concentration is about 0.025M. The pH of the solution is at a pH of from about 6.0 to about 8.0. The column is washed with the buffered $CaCl_2$ solution until all the Factor VIII complex is washed from the column. Typically, from about 2 to about 4 column-volumes of the buffered $CaCl_2$ solution are applied to the column to elute Factor VIII complex. When the concentration of $CaCl_2$ is less than about 0.05M, less than a desirable amount of Factor VIII complex is eluted from the heparin-coupled chromatographic medium. When the concentration of $CaCl_2$ is greater than about 0.2M, unwanted proteins are eluted along with the Factor VIII complex, thereby reducing the specific activity of Factor VIII complex in the final product. Also, salt concentrations greater than 0.2M can lead to dissociation of the Factor VIII complex, which results in the Factor VIII:C being less stable. Preferably, the concentration of $CaCl_2$ is about 0.1M, to maximize the amount of Factor VIII complex eluted but to minimize elution of unwanted proteins and dissociation of the Factor VIII complex.

When the concentration of histidine is greater than about 0.035M, the high concentrations are wasteful of the histidine. Histidine concentrations less than about 0.015M have insufficient buffering capacity to ensure that the pH remains at the desired level.

The Factor VIII complex eluted from the heparin-coupled chromatographic medium is concentrated 10 to 15 fold by ultra-filtration, using an ultrafilter (or its equivalent) such as that supplied under the trade name of "CENTRASETTE" Omega 100K cassette, by Filtron.

Separation of Factor VIII Complex by Affinity Chromatography in a Batch Process

In an exemplary embodiment of the practice of this invention, Factor VIII complex solution from the viral inactivation step (the Factor VIII complex containing impure protein fraction) is applied directly to the washed heparin-coupled chromatographic medium and mixed for about 30 min. to about 45 min. for batch processing. During this time, the Factor VIII complex binds to the heparin ligand on the chromatographic medium, leaving a supernatant containing proteins other than Factor VIII complex in solution. The chromatographic medium is removed by decanting the supernatant, and the medium is then washed to remove unbound proteins. In one exemplary embodiment, the washing is effected by resuspending the Factor VIII complex-bound, heparin-coupled chromatographic medium in about 5 to 10 volumes of a solution comprising about 0.015M to 0.035M buffer, such as histidine, pH 6.5 to 7.5, comprising a salt solution, such as LiCl, NaCl, or KCl, at a concentration of about 0.1M to about 0.15M. Preferably, the solution comprises 0.025M histidine at a pH of 6.8 comprising 0.15M NaCl. The Factor VIII complex-bound, heparin-coupled chromatographic medium is removed from the wash solution by decanting the supernatant, i.e., the wash solution. The Factor VIII complex remains bound to the heparin-coupled chromatographic medium throughout the wash procedure.

Factor VIII complex is eluted from the heparin-coupled chromatographic medium by applying to the medium a buffered aqueous solution incorporating calcium, magnesium, strontium, or other divalent metal-ion salt, such as $CaCl_2$, $MgCl_2$, $SrCl_2$, or the like, and histidine. Preferably, the eluting agent is $CaCl_2$ at a concentration of from about 0.01M to about 0.3M, and about 0.015M about 0.035M histidine. More preferably, the $CaCl_2$ is at a concentration of from about 0.05M to about 0.2M, and the histidine concentration is from about 0.02M to 0.03M, and most preferably, the $CaCl_2$ is at a concentration of about 0.1M, and the histidine concentration is about 0.025M. The solution is at a pH of from about 6.0 to about 8.0. The medium is washed with the buffered $CaCl_2$ solution by resuspending the medium in the buffer and separating the medium from the buffer by centrifugation. The wash is repeated until substantially all of Factor VIII:C is recovered from the heparin chromatography medium. When the concentration of $CaCl_2$ is less than about 0.05M, less than a desirable amount of Factor VIII complex is eluted from the heparin-coupled chromatographic medium. When the concentration of $CaCl_2$ is greater than about 0.2M, unwanted proteins are eluted along with the Factor VIII complex, thereby reducing the specific activity of Factor VIII complex in the final product. Also, salt concentrations greater than 0.2M can lead to dissociation of the Factor VIII complex, which results in the Factor VIII:C being less stable. Preferably, the concentration of $CaCl_2$ is about 0.1M, to maximize the amount of Factor VIII complex eluted but to minimize elution of unwanted proteins and dissociation of the Factor VIII complex.

The Factor VIII complex eluted from the heparin-coupled chromatographic medium is washed by ultrafiltration, using an ultrafilter (or its equivalent) such as that supplied under the trade name of "CENTRASETTE" Omega 100K cassette.

Purification of Factor VIII complex by Glycine/NaCl Precipitation

The Factor VIII complex in the ultrafiltered material is precipitated by the addition of glycine and NaCl. The glycine/NaCl is an effective means of increasing the specific activity of the Factor VIII complex. However, it is important that this step be included after the heparin chromatography step, or other suitable partial purification step, since its inclusion at an earlier step results in a "milky" solution, thereby causing the precipitation of undesirable components from the solution, in addition to Factor VIII. The fractions recovered from the heparin chromatography medium are brought to about 1.5M to about 2.5M glycine and about 1M to about 2M NaCl. The solution is mixed at about 15° to about 25° C. for about two hours, and the precipitate which forms is collected by centrifugation. Preferably, 2M glycine and 1.3M NaCl are added to the fractions recovered from the heparin chromatography medium.

The precipitate, which contains Factor VIII complex, is washed with a wash solution comprising about 0.025M histidine, pH 6.8, 2M glycine, and 1.3M NaCl, and is collected by centrifugation. The wash procedure results in the resolubilization of contaminating proteins caught in the glycine/NaCl precipitate but not the Factor VIII complex. The wash procedure is then repeated, if desired, and the final precipitate is collected by centrifugation or filtration and dissolved in a buffer comprising about 0.025M histidine, 0.1M arginine, pH 6.0 to 8.0. After the precipitate is dissolved, about 0.02 to about 1% (wt/vol) albumin is added as a bulking agent if desired, and the solution is filtered.

The solution is then divided among separate vials, with each vial containing a desired number of units of Factor VIII:C activity. The solutions are then lyophilized to provide separate vials of purified Factor VIII complex concentrate.

EXAMPLE 1

Preparation of an Impure Protein Fraction Containing Factor VIII

Forty grams of cryoprecipitate was dissolved in 120 ml of distilled water containing about 80 units of heparin per ml of water. The heparin solution was mixed at a temperature of about 30° C. until the cryoprecipitate was completely dissolved (approximately 10 minutes), to provide a cryoprecipitate/heparin solution. After the cryoprecipitate was dissolved, the pH of the cryoprecipitate/heparin solution was adjusted to about pH 7.0 using 0.1M HCl, and the solution was stirred for an additional 20 to 30 minutes.

An aqueous PEG solution comprising about 31.5% (wt/vol) PEG, 0.22% (wt/vol) sodium citrate dihydrate, and 0.08% (wt/vol) citric acid monohydrate, at a pH of 6.2, was then added to the cryoprecipitate/heparin solution to give a final concentration of 3.5% (wt/vol) PEG. The pH of the PEG/cryoprecipitate/heparin solution was adjusted to about 6.3 with dilute acetic acid. The pH-adjusted solution was mixed for approximately 15 minutes, at a temperature of about 27° C. The addition of PEG resulted in precipitation of various contaminating proteins from the Factor VIII complex which remained in solution.

The PEG precipitate was separated from the Factor VIII complex-containing supernatant solution by centrifugation. The supernatant, i.e., the Factor VIII complex containing impure protein fraction, was recovered. The supernatant was then treated to inactivate viruses which may be present in the blood products, by adding a solution containing about 0.3% (wt/vol) tri-n-butylphosphate and about 1% (wt/vol) TWEEN-80, and incubating at 25° C. for about 6 hrs.

The viral-inactivated supernatant solution, i.e., the viral-inactivated Factor VIII complex containing impure protein fraction, was clarified by filtration, and was then recovered for further purification of Factor VIII complex by affinity chromatography on a heparin-coupled chromatographic medium.

EXAMPLE 2

Purification of Factor VIII Complex by Heparin Affinity Chromatography

An impure protein fraction prepared by a process such as the process described in Example 1, containing a total of 1,000 units of Factor VIII:C activity, was applied to heparin-coupled chromatography medium packed into a column, and the flow rate of the column was maintained at 2 ml per min. The column effluent was collected, and the column was washed with 600 ml of 0.025M histidine, pH 6.8, containing 0.15M NaCl. Elution of Factor VIII complex was achieved with 200 ml of 0.1M $CaCl_2$ and 0.025M histidine, pH 6.8. All effluent and eluate samples are assayed for Factor VIII:C blood-clotting activity using a COAG-A-MATE XC clotting machine.

EXAMPLE 3

Glycine/NaCl Precipitation of Factor VIII

Factor VIII complex prepared in accordance with a process such as that shown in Example 2 was concentrated using a "CENTRASETTE," Omega 100K cassette. The concentrated solution was then brought to 2M glycine and 0.83M NaCl and mixed at 25° C. for 2 hours. The glycine/NaCl precipitate which formed was collected by centrifugation and washed with 100 ml of a wash solution comprising 0.025M histidine, pH 6.8, 2M glycine, and 1.3M NaCl. The washed precipitate was again collected by centrifugation, and the wash procedure was repeated. The final washed precipitate was dissolved in 10 ml buffer comprising about 0.025M histidine, 0.1M arginine, pH 7.0 to 7.6. After the precipitate was dissolved, 0.2% (wt/vol) albumin was added, and the solution was filtered. The resultant solution was then assayed for Factor VIII:C blood clotting activity using a COAG-A-MATE XC clotting machine. The concentration of fibronectin in the final precipitate was also analyzed. The results are summarized in Table I.

EXAMPLE 4

The procedure of Example 3 was repeated, except that 2M glycine and 1.3M NaCl were used to form the glycine/NaCl precipitate. The resultant solution was then assayed for Factor VIII:C blood clotting activity using a COAG-A-MATE XC clotting machine. The concentration of fibronectin in the final precipitate was also analyzed. The results are summarized in Table I.

EXAMPLE 5

The procedure of Example 3 was repeated, except that 2M glycine and 1.38M NaCl were used to form the glycine/NaCl precipitate. The resultant solution was then assayed for Factor VIII:C blood clotting activity using a COAG-A-MATE XC clotting machine. The concentration of fibronectin in the final precipitate was also analyzed. The results are summarized in Table I.

EXAMPLE 6

The procedure of Example 3 was repeated, except that 2M glycine and 1.56M NaCl were used to form the glycine/NaCl precipitate. The resultant solution was then assayed for Factor VIII:C blood clotting activity using a COAG-A-MATE XC clotting machine. The concentration of fibronectin in the final precipitate was also analyzed. The results are summarized in Table I.

EXAMPLE 7

The procedure of Example 3 was repeated, except that 2M glycine and 1.93M NaCl were used to form the glycine/NaCl precipitate. The resultant solution was then assayed for Factor VIII:C blood clotting using a COAG-A-MATE XC clotting machine. The concentration of fibronectin in the final precipitate was also analyzed. The results are summarized in Table I.

TABLE I

| | % Yield in Precipitate[1] Factor VIII | % Yield in Precipitate Fibronectin | Specific Activity Factor VIII[2] |
|---|---|---|---|
| 0.83 M NaCl* | 2 | <1 | 69 |
| 1.30 M NaCl | 62 | 2 | 94 |
| 1.38 M NaCl | 103 | 4 | 84 |
| 1.56 M NaCl | 91 | 14 | 56 |
| 1.93 M NaCl | 95 | 28 | 40 |

*The experiments were performed in the presence of the NaCl concentration indicated and 2 M glycine.
[1] % yield in the precipitate is the activity of Factor VIII:C in the precipitate divided by the activity of Factor VIII:C contained in the cryoprecipitate multiplied by 100.
[2] Factor VIII:C units/mg protein.

EXAMPLE 8

After 9,030 kg of plasma were cryoprecipitated, the resultant 107 kg of cryoprecipitate was dissolved in 320 l of distilled water containing about 120 units of heparin per ml of water. The heparin solution was mixed at a temperature of about 30° C. until the cryoprecipitate was completely dissolved (approximately 10 min.), to provide a cryoprecipitate/heparin solution. After the cryoprecipitate was dissolved, the pH of the cryoprecipitate/heparin solution was adjusted to about 7 using 0.1M HCl, and the solution was stirred for an additional 20 to 30 min.

An aqueous PEG solution comprising about 31.5% (wt/vol) PEG, 0.22% (wt/vol) sodium citrate dihydrate, and 0.08% (wt/vol) citric acid monohydrate, at a pH of 6.2, was then added to the cryoprecipitate/heparin solution to give a final concentration of 3.5% (wt/vol) PEG. The pH of the PEG/cryoprecipitate/heparin solution was adjusted to about 6.3 with dilute acetic acid. The pH-adjusted solution was mixed for approximately 15 minutes, at a temperature of about 27° C. The addition of PEG resulted in precipitation of various contaminating proteins from the Factor VIII complex, which remained in solution.

The PEG precipitate was separated from the Factor VIII complex-containing supernatant solution by centrifugation. The PEG supernatant, i.e., the Factor VIII complex containing impure protein fraction, was recovered. The supernatant was then treated to inactivate viruses which may be present in the blood products, by the addition of a solution containing about 0.3% (wt/vol) tri-n-butylphosphate and about 1% (wt/vol) TWEEN-80 and incubating at 25° C. for about 6 hrs.

The viral-inactivated supernatant solution, i.e., the viral-inactivated Factor VIII complex containing impure protein fraction, was clarified by filtration and then recovered for further purification of Factor VIII complex by affinity chromatography on a heparin-coupled chromatographic medium.

The Factor VIII complex-containing solution was applied to a 200 liter (l) heparin-coupled chromatographic medium packed into the column. The column effluent was collected, and the column was washed with 1700 l of 0.025M histidine, pH 6.8, containing 0.10M NaCl. Elution of Factor VIII complex was achieved with 600 l of 0.1M $CaCl_2$ and 0.025M histidine, pH 6.8.

The eluate from a heparin column (the column eluate) was concentrated 15 fold using a CENTRASETTE, Omega 100K cassette. The concentrated solution, i.e. the eluate concentrate, was then brought to 2M glycine and 1.2M NaCl and mixed at 25° C. for 2 hours. The precipitate which formed was collected by centrifugation and washed with a wash solution comprising 0.025M histidine, pH 6.8, 2M glycine, and 1.3M NaCl. The washed precipitate was collected by filtration. The washed precipitate was dissolved in 2 l buffer comprising about 0.025M histidine, 0.1M arginine, pH 7.0 to 7.6. After the precipitate was dissolved, 0.5% (wt/vol) albumin was added, and the solution was filtered.

The resultant solution was then assayed for Factor VIII:C blood clotting activity using a COAG-A-MATE XC clotting machine. The results are summarized in Table II.

TABLE II

| Sample | Units[1] × $10^{-3}$ | Units/kg Plasma | Specific Activity Units/mg |
|---|---|---|---|
| Plasma | 9,030 | 1,000 | 0.01 |
| Cryoprecipitate | 3,540 | 392 | 0.7 |
| PEG-supernatant | 3,645 | 404 | 1.5 |
| Column eluate | 2,640 | 292 | — |
| Eluate Conc. | 1,540 | 171 | 14.5 |
| Glycine/NaCl | 782 | 87 | 99.1 (16.5)* |

*Specific activity after addition of HSA.
[1] Units of Factor VIII:C activity.

The resultant purified Factor VIII complex solution was further analyzed to evaluate the contaminating proteins present. The results are summarized in Table III.

TABLE III

| Specific Activity (Factor VIII:C units/mg) | 99.1 |
|---|---|
| Fibronectin (μg/unit*) | 1.5 |
| Fibrinogen (μg/unit*) | <0.8 |
| IgG (μg/unit*) | <0.1 |
| IgM (μg/unit*) | ≦0.1 |
| HSA (μg/unit*) | <0.1 |

*per unit of Factor VIII:C.

EXAMPLE 9

Comparison of Various Preparations of Factor VIII

A number of Factor VIII complex preparations were made in accordance with the procedure of Example 8. The purified samples were analyzed for Factor VIII:C specific activity and also for contamination with fibronectin, fibrinogen and IgM. The results obtained from these purifications are summarized in Table IV.

TABLE IV

| | Factor VIII:C | | | | |
|---|---|---|---|---|---|
| Lot No. | Yield units/kg Plasma | Specific Activity[1] units/mg[2] | Fibronectin μg/unit* | Fibrinogen μg/unit* | IgM μg/unit* |
| 1 | 194 | 68.8 | 0.5 | 3.8 | 0.13 |
| 2 | 164 | 77.3 | 0.53 | <0.5 | <0.02 |
| 3 | 174 | 91.9 | 0.48 | 0.44 | <0.02 |
| 4 | 178 | 110.2 | 0.43 | <0.66 | <0.03 |
| 5 | 140 | 108.0 | n.m. | n.m. | n.m. |

*per unit of Factor VIII
n.m. = not measured
[1] Factor VIII:C/mg protein
[2] The variation in the specific activity level is due to inexperience with and development of the new purification for Factor VIII. Specific activities of at least 100 are now routinely obtained.

The above descriptions of exemplary embodiments of processes for producing Factor VIII complex concentrates are for illustrative purposes. Because of variations which will be apparent to those skilled in the art, the present invention is not intended to be limited to the particular embodiments described above. This invention can also be practiced in the absence of any element not specifically disclosed. The scope of the invention is defined by the following claims.

What is claimed is:

1. A process for separating Factor VIII complex from an impure protein fraction containing Factor VIII complex, the process comprising the steps of:
   providing an aqueous solution of an impure protein fraction comprising Factor VIII complex;
   applying the impure protein fraction solution to a heparin-coupled chromatographic medium to thereby bind Factor VIII complex to the heparin;
   eluting the Factor VIII complex from the chromatographic medium using an aqueous solution comprising $CaCl_2$;
   adding a sufficient amount of glycine and sodium chloride to the eluate to thereby precipitate Factor VIII complex;
   washing the Factor VIII complex precipitate with a wash solution; and
   recovering the washed Factor VIII complex.

2. The process of claim 1 wherein the $CaCl_2$ is present in the solution at a concentration of from about 0.01M to about 0.3M.

3. The process of claim 1 wherein the aqueous $CaCl_2$ solution further comprises histidine at a concentration of from about 0.015M to about 0.035M.

4. The process of claim 3 wherein the concentration of histidine is about 0.025M.

5. The process of claim 3 wherein the aqueous $CaCl_2$ solution has a pH of from about 6.0 to 8.0.

6. The process of claim 5 wherein the pH is maintained at about 6.8.

7. The process of claim 1 wherein the Factor VIII complex is precipitated from the eluate with about 1.5M to about 2M glycine and about 1M to about 2M sodium chloride.

8. The process of claim 1 wherein the Factor VIII complex is precipitated from the eluate with about 2M glycine and about 1.3M sodium chloride.

9. The process of claim 1 wherein the wash solution comprises about 0.025M histidine, pH 6.8, 2M glycine, and 1.3M sodium chloride.

10. The process of claim 1 wherein the impure protein fraction containing Factor VIII complex is derived from cryoprecipitate.

11. The process of claim 1 wherein the impure protein fraction is applied to the heparin-coupled chromatographic medium in a batch process.

12. A process for separating Factor VIII complex from an impure protein fraction containing Factor VIII complex, comprising the steps of:
   providing an aqueous solution of an impure protein fraction containing Factor VIII complex;
   applying the impure protein fraction solution to a chromatographic medium comprising a heparin ligand coupled to a resin;
   binding Factor VIII complex to the heparin ligand on the chromatographic medium;
   eluting the Factor VIII complex from the chromatographic medium using an aqueous solution comprising $CaCl_2$ as the eluting agent;
   precipitating the Factor VIII complex from the eluate with glycine and sodium chloride;
   washing the precipitate with a wash solution; and
   dissolving the Factor VIII complex precipitate in an aqueous solution to provide a Factor VIII complex solution with a specific activity, with respect to the Factor VIII:C activity, of about 70 to about 150 units/mg.

13. The process of claim 12 wherein the concentration of $CaCl_2$ in the aqueous solution is from about 0.05M to about 0.2M.

14. The process of claim 12 wherein the aqueous $CaCl_2$ solution has a pH of from about 6.0 to 8.0.

15. The process of claim 14 wherein the pH is maintained at about 6.8.

16. The process of claim 12 wherein the aqueous $CaCl_2$ solution includes histidine at a concentration of from about 0.015M to about 0.035M.

17. The process of claim 16 wherein the concentration of histidine is about 0.025M.

18. The process of claim 12 wherein the Factor VIII complex is precipitated with about 1.5M to about 2M glycine and about 1M to about 2M sodium chloride.

19. The process of claim 12 wherein the Factor VIII complex is precipitated with about 2M glycine and about 1.3M sodium chloride.

20. The process of claim 12 wherein the wash solution comprises about 0.025M histidine, pH 6.8, 2M glycine, and 1.3M sodium chloride.

21. The process of claim 12 wherein the impure protein fraction containing Factor VIII is derived from cryoprecipitate.

* * * * *

UNITED STATES PATENT AND TRADEMARK OFFICE
CERTIFICATE OF CORRECTION

PATENT NO. : 5,288,853

DATED : February 22, 1994

INVENTOR(S) : Prabir Bhattacharya; Toshiharu Motokubota

It is certified that error appears in the above-indentified patent and that said Letters Patent is hereby corrected as shown below:

On the title page: Item

[75] Inventors: change "Prabir Bhattacharva" to -- Prabir Bhattacharya --.
Item [19] change "Bhattacharva" to --Bhattacharya --.

Column 3, line 1, change "DRAWING" to -- DRAWINGS --.
Column 3, lines 25,26, after "precipitation" delete "step results in a".
Column 3, line 31, after "precipitation" insert -- step results in a --.

Column 4, line 62, after "sold" delete "by".

Column 8, line 43, after "0.015M" insert -- to --.
Column 8, line 46, after "0.02M to" insert -- about --.

UNITED STATES PATENT AND TRADEMARK OFFICE
CERTIFICATE OF CORRECTION

PATENT NO. : 5,288,853
DATED : February 22, 1994
INVENTOR(S) : Prabir Bhattacharya; Toshiharu Motokubota It is certified that error appears in the above-indentified patent and that said Letters Patent is hereby corrected as shown below:

Column 3, line 1, change "DRAWING" to -- DRAWINGS --.
Column 3, lines 25,26, after "precipitation" delete "step results in a".
Column 3, line 31, after "precipitation" insert -- step results in a --.

Column 4, line 62, after "sold" delete "by".

Column 8, line 43, after "0.015M" insert -- to --.
Column 8, line 46, after "0.02M to" insert -- about --.

Signed and Sealed this

Fourth Day of April, 1995

Attest:

BRUCE LEHMAN

*Attesting Officer*    *Commissioner of Patents and Trademarks*